(12) United States Patent
Luginbuehl

(10) Patent No.: US 8,163,033 B2
(45) Date of Patent: Apr. 24, 2012

(54) PROSTHETIC DEVICE FOR CARTILAGE REPAIR

(75) Inventor: Reto Luginbuehl, Bettlach (CH)

(73) Assignee: Dr. H.C. Robert Mathys Stifung, Bettlach (CH)

( * ) Notice: Subject to any disclaimer, the term of this patent is extended or adjusted under 35 U.S.C. 154(b) by 955 days.

(21) Appl. No.: 10/561,878

(22) PCT Filed: Jun. 17, 2004

(86) PCT No.: PCT/EP2004/006530
§ 371 (c)(1),
(2), (4) Date: Feb. 7, 2007

(87) PCT Pub. No.: WO2005/000169
PCT Pub. Date: Jan. 6, 2005

(65) Prior Publication Data
US 2007/0244484 A1   Oct. 18, 2007

(30) Foreign Application Priority Data
Jun. 24, 2003   (EP) .................................... 03014191

(51) Int. Cl.
*A61F 2/02* (2006.01)
*A61F 2/30* (2006.01)

(52) U.S. Cl. .................................. 623/23.72; 623/14.12
(58) Field of Classification Search ............... 623/23.72, 623/14.12
See application file for complete search history.

(56) References Cited

U.S. PATENT DOCUMENTS

| 4,553,272 | A | * | 11/1985 | Mears | 623/1.4 |
|---|---|---|---|---|---|
| 5,607,474 | A | | 3/1997 | Athanasiou et al. | 623/11 |
| 5,624,463 | A | | 4/1997 | Stone et al. | 623/18 |
| 6,511,511 | B1 | | 1/2003 | Slivka et al. | 623/23.75 |
| 6,626,945 | B2 | | 9/2003 | Simon et al. | 623/17.19 |
| 6,626,950 | B2 | | 9/2003 | Brown et al. | 623/23.72 |
| 2002/0183857 | A1 | * | 12/2002 | Yang | 623/23.72 |
| 2003/0023318 | A1 | * | 1/2003 | Simmoteit et al. | 623/23.76 |
| 2003/0075822 | A1 | * | 4/2003 | Slivka et al. | 264/45.3 |

* cited by examiner

*Primary Examiner* — Bruce E Snow
*Assistant Examiner* — Melissa Hoban
(74) *Attorney, Agent, or Firm* — Ohlandt, Greeley, Ruggiero & Perle, LLP

(57) ABSTRACT

A prosthetic device for repairing or replacing cartilage or cartilage-like tissue is described. The prosthetic device comprises at least one layer of highly oriented fibers, a base component and a stabilization area provided in between. Said fibers are aligned to more than 50% in a direction perpendicular to the base component.

32 Claims, 1 Drawing Sheet

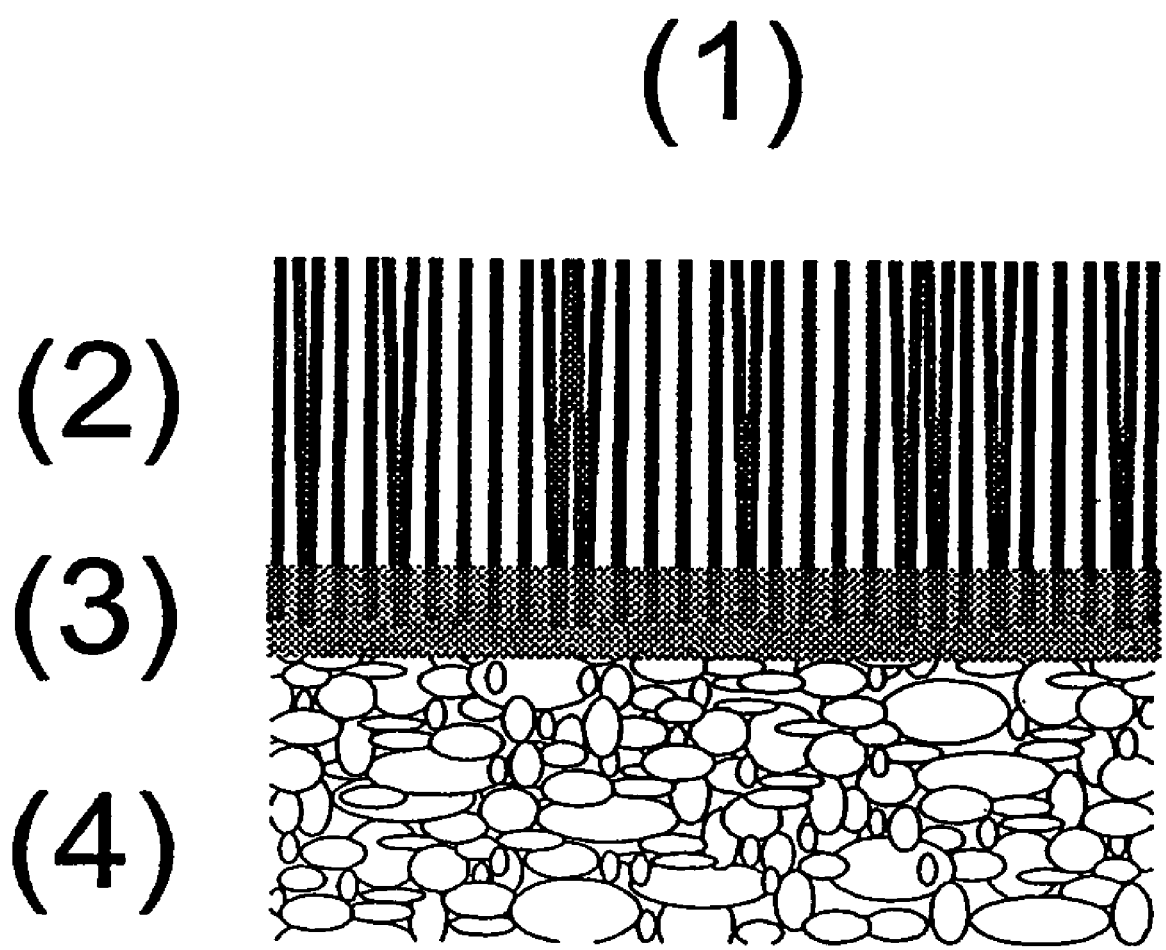

PROSTHETIC DEVICE FOR CARTILAGE REPAIR

CROSS-REFERENCES TO RELATED APPLICATIONS

The present application is claiming priority of European Patent Application No. 03 014 191.5, filed on Jun. 24, 2003 and PCT International Application No. PCT/EP2004/006530, filed on Jun. 17, 2004 the content of which is herein incorporated by reference.

BACKGROUND OF THE INVENTION

1. Field of the Invention

The present invention is directed to a prosthetic device for repairing or replacing cartilage or cartilage-like tissues. Said prosthetic devices are useful as articular cartilage substitution material and as scaffold for regeneration of articular cartilagenous tissues.

2. Description of the Related Art

Articular cartilage tissue covers the ends of all bones that form diarthrodial joints. The resilient tissues provide the important characteristic of friction, lubrication, and wear in a joint. Furthermore, it acts as a shock absorber, distributing the load to the bones below. Without articular cartilage, stress and friction would occur to the extent that the joint would not permit motion. Articular cartilage has only a very limited capacity of regeneration. If this tissue is damaged or lost by traumatic events, or by chronic and progressive degeneration, it usually leads to painful arthrosis and decreased range of joint motion.

Several methods have been established in the last decades for the treatment of injured and degenerated articular cartilage. Osteochondroal transplantation, microfracturing, heat treatment for sealing the surface, shaving, autologous chondrocyte transplantation (ACT), or total joint replacement are among the common techniques applied in today's orthopedic surgery.

Joint replacement techniques where metal, ceramic and/or plastic components are used to substitute partially or totally the damaged or degenerated joint have already a long and quite successful tradition. The use of allograft material has been successful to some extent for small transplants, however, good quality allografts are hardly available.

Osteochondroal transplantation (i.e. mosaicplasty) or autologous chondrocyte transplantation (ACT) are applied whenever total joint replacement is not yet indicated. These methods can be used to treat small and partial defects in a joint. In mosaicplasty defects are filled with osteochondral plugs harvested in non-load bearing areas. In ACT, chondrocytes are harvested by biopsy and grown in-vitro before a highly concentrated cell suspension is injected below an membrane (artificial or autologous) covering the defect area.

Commonly, the replacement of cartilage tissue with solid permanent artificial inserts has been unsatisfactorily because the opposing articular joint surface is damaged by unevenness or by the hardness of the inserts. Therefore, the transplantation technology had to take a step forward in the research of alternative cartilage materials such as biocompatible materials and structures for articular cartilage replacement.

For example, U.S. Pat. No. 5,624,463 describes a prosthetic articular cartilage device comprising a dry, porous volume matrix of biocompatible and at least bioresorbable fibers and a base component. Said matrix establishes a bioresorbable scaffold adapted for the ingrowth of articular chondrocytes and for supporting natural articulating joint forces. Useful fibers include collagen, reticulin, elastin, cellulose, alginic acid, chitosan or synthetic and biosynthetic analogs thereof. Fibers are ordered in substantially circumferentially extending or substantially radially extending orientations. The base component is provided as a support on which the fiber matrix is applied. It is configured to fit in a complementary aperture in defective bone to secure the position of such a device in the bone. The base component is a composite material comprising a dispersion of collagen and composition consisting of tricalcium phosphate and hydroxyapatite.

It has been shown, however, that the function of the above construction has not been always satisfactory. The reason is that said known prosthetic articular cartilage device is frequently unstable due to its structure and thus had to be replaced in the joint area by another surgical operation in to again repair cartilage joints such as knee and hip.

In view of this situation, in the field of articular cartilage replacement materials, there is a need for a structure suitable as a prosthetic articular cartilage which is made of natural resorbable materials or analogs thereof and having an improved structure stability and an accurate positioning in the bone. At the same time, the prosthetic device should be biomechanically able to withstand normal joint forces and to promote repair and replacement of cartilage tissue or cartilage-like tissue.

SUMMARY OF THE INVENTION

These objects are solved by the prosthetic device according to the present invention.

The present invention relates to a prosthetic device for repairing or replacing cartilage or cartilage-like tissue which comprises at least one layer comprising oriented fibers, a base component to anchor said fibers in subchondral environment and a stabilization area provided between said at least one layer of fibers and said base component, wherein said fibers are aligned essentially parallel to an insertion axis of the base component, i.e. perpendicularly to the plane of the articulating surface.

According to a further aspect of the invention a prosthetic device for repairing or replacing cartilage or cartilage-like tissue is proposed which comprises at least one layer comprising fibers, a base component to anchor said fibers in subchondral environment and a stabilization area provided between fibers and said base component, wherein between the base component and the fibers a cell barrier layer is provided.

The preferred embodiments of the prosthetic device of the present invention are also provided.

It has been surprisingly found that the stability of a prosthetic articular cartilage device can be essentially improved by providing a stabilization area between said at least one layer of fibers and said base component and by a specific alignment of said fibers e.g. to more than 50% in parallel to the insertion axis of the base component, usually in a direction perpendicular to a top surface of the base component facing the fibers. The stabilization area allows to hold together the base component and the fibers by acting as a "adhesive component". The specific alignment of the fibers in the layer perfectly mimics the cartilage and cartilage-like tissues providing an excellent mechanical stability. At the same time a basis for the ingrowth of articular chondrocytes is provided resulting in a rapid cartilage growth, thus assuring a long term cartilage replacement.

The invention itself may be more fully understood from the following description when read together with the accompanying drawing in which the only FIGURE shows a cross-sectional view of an embodiment of the prosthetic device of the invention.

BRIEF DESCRIPTION OF THE DRAWINGS

In the only FIGURE a preferred form of a prosthetic device (1) embodying the invention is shown.

DETAILED DESCRIPTION OF THE INVENTION

The device (1) includes at least one layer comprising oriented fibers of the biocompatible and/or at least partially resorbable material (2), a stabilization area 3, and a base component of a bone substitute material (4).

As can be seen from the FIGURE, the fibers (2) are essentially aligned in a direction perpendicular to a top surface of the base component (4), which top surface faces the fibers. The fibers thus form a brush-like structure in a direction perpendicular to the base component (4). The fibers (2) can be aligned to more than 50% in a direction perpendicular to the top surface of the base component (4). An alignment of more than 90% in a direction perpendicular to the base component (4) is preferred. The fibers (2) may change alignment direction and self-organize at the uppermost end of the brush like structure. This might occur under pressure after implantation.

In principle, any material can be used for the fibers (2) as long as they are biocompatible. Preferably the material is also biodegradable. In order to enhance the stability of the structure (2) a portion of material of the fibers may be cross-linked. In one preferred embodiment of the invention the fibers (2) include a mineral material, synthetic polymers or molecules, natural polymers or molecules, biotechnologically derived polymers or molecules, biomacromolecules, or any combination thereof.

The fibers (2) themselves are not limited to any structure. They may be straight, twisted, curled, or of any tertiary structure It is also possible to use a combination thereof. Additionally, the fibers (2) themselves can be linear, branched or grafted.

According to the invention, the shape and character of the fibers (2) can be homogeneous or comprise a combination of various fibers the previously mentioned different forms, including chemical, physical composition, and origin. The fiber-to-fiber anchoring distance can be varied within a broad range, i.e. between 1 nm to 1 mm, with a preferred fiber-to fiber anchoring distance of 1 µm to 100 µm. The distances themselves can be homogeneous or heterogeneous. Examples of heterogeneous distances are gradient-like distributions, or random distributions, or specific pattern alignment, or any combination thereof.

The fibers (2) of the device of the present invention can be provided as mono-filament or multi-filament fibers of any length. Fiber arrangement in a woven, non-woven twisted, knitted, or any combination thereof is possible. If desired, the lateral cross-section of the fibers (2) can be solid or hollow.

According to the invention, the fiber diameter may be varied in a broad range. Advantageously, a range of 50 nm to 1 mm is proposed. Preferably, the fiber diameter is in range of 1 µm to 250 µm.

According to the invention, the fibers (2) may have a flexible structure or a rigid structure depending on the final use of the device (1). In case of adapting to the articulation of a joint or opposing tissue, the fibers (2) should form a flexible structure.

In case of using mineral fibers for the layer of highly oriented fibers (2), a selection may be made from synthetic or natural materials with a glass-like structure, crystalline structure, or any combination thereof.

The fiber material is usually homogeneous. Depending on the final use of the device of the invention (1), the fiber material can also be heterogeneous, i.e., selected from various materials or it can comprise an engineered combination of the materials as mentioned above.

In some instances, however, the fibers (2) can be coated or grafted with one or more of the previously mentioned materials.

In various forms of the invention, the fiber material(s) can have a liquid absorbing capacity by interactions with a solvent. Preferably, the liquid absorbing capacity is in a range of 0.1 to 99.9%, a range of 20.0 to 99.0% being particularly preferred.

Usually, the liquid to be absorbed by the fibers (2) is water and/or body fluid available at the position where the device (1) is implanted. When absorbing water and/or body fluids, the fibers (2) advantageously form a gel or transform to a gel-like state.

Upon uptake of water and/or body fluids the fibers (2) can swell and, therefore, an internal pressure within the fiber component is built up. That pressure helps stabilizing the structure. Furthermore, externally added components including cells are entrapped under the pressure within the fiber structure as in a natural cartilage.

It has been shown that one layer of fibers (2) already brings about good results. However, in some instances, it can be advisable to provide a couple of layers of fibers which is/of course/dependent on the final use of the device of the invention (1). The assembly of multiple layer structures can be a head-head, head-tail, or tail-tail, and any combination thereof. It can also be an intercalated assembly wherein the clear interface border is lost between the different layers and gets continuous.

The device of the present invention (1) comprises/as a further essential structural component/a base component (4). The function of the base component (4) is to anchor the fibers (2) in subchondral environment. This subchondral anchor function helps to keep the device (1) in place when implanted. The base component (4) can be of variable size and shape. Preferably, the shape of the base component (4) is round cylindrical or conical. The diameter of the base component (4) can vary in stepwise manner or in a continuous transition zone of any size. In practice/the diameter is related to the defect size and ranges between 2 and 30 mm, with a total height being 1 to 30 mm. The top surface of the base component (4) is usually either flat or it mimics the shape of the subchondral plate or the cartilage surface to be replaced.

The material of the base component (4) of the device of the invention (1) can be a material, which is normally used as a bone substitute. Examples of the material are those as listed above in connection with the material of the fibers (2). If desired, the material for the base component (4) is a synthetic ceramic. The ceramic can be selected out of one or several of the following groups: calcium phosphates, calcium sulfates, calcium carbonates, or any mixture thereof.

If the base component (4) of the device (1) is a calcium-phosphate, one of the following compositions groups is preferred: di-calciumphosphatedihydrate ($CaHPO_4 \times 2H_2O$), dicalciumphosphate ($CaHPO_4$), alpha-tricalciumphosphate (alpha-$Ca_3(PO_4)_2$), beta-tricalciumphosphate (beta$Ca_3(PO_4)_2$), calcium deficient hydroxylapatite ($Ca_9(PO_4)5(HPO_4)OH$), hydroxylapatite ($Ca_{10}(PO_4)_6OH_2$), carbonated apatite ($Ca_{10}(PO_4)_3(CO_3)_3$) ($OH)_2$), fluorapatite ($Ca_{10}(PO_4)_6(F,OH)_2$)' chlorapatite ($Ca_{10}(PO_4)_6(Cl,OH)_2$), whitlockite ((Ca,Mg)$_3(PO_4)_2$), tetracalciumphosphate ($Ca_4(PO_4)_2O$), oxyapatite ($Ca_{10}(PO_4)_6O$), beta-calciumpyrophosphate (beta-$Ca_2$ ($P_2O_7$)), alpha-calciumpyrophosphate, gamma-calciumpyrophosphate, octacalciumphosphate ($Ca_8H_2(PO_4)_6 \times 5H_2O$).

It is also possible to have the above mentioned mineral materials doped or mixed with metallic, semimetallic, and/or non-metallic ions, preferably magnesium, silicon, sodium, potassium, strontium and/or lithium.

In another preferred embodiment of the invention, the material of the base component (4) is a composite material comprising a mineral, inorganic, organic, biological, and/or biotechnological derived non-crystalline component and a mineral crystalline component. The non-crystalline components are often of polymeric nature.

In a preferred embodiment of the invention, the structure of the materials of the base component (4) is highly porous with interconnecting pores. This would allow any substances and cell in the subchondral environment to diffuse or migrate, respectively, into the base component (4).

The third component of the device of the invention (1) is the stabilization area (3) which is provided between said at least one layer of fibers (2) and said base component (4). This stabilization area (3) provides a mechanical, physical or chemical link between the two other essential elements of the device of the invention (1). Another function of the stabilization area (3) is to stabilize and hold in-place the fibers (2) in the specific brush-like arrangement as mentioned above. This can be accomplished by e.g. knitting, weaving, grafting, gluing, embedding, or another mechanical, physical or chemical method. The interaction between the fibers (2) and the stabilization area (3) can be of physical/mechanical, electrostatic or covalent chemical nature, or a combination thereof.

In a preferred embodiment of the invention, the stabilization area (3) is comprised of an additional material, a chemical substance, the base component (4) material itself, or the fibers themselves or any combination thereof. Depending on the final use of the device of the invention (1), the stabilization system (3) is located at one end, at both ends or somewhere in between the two ends of the fibers (2).

Another function of the stabilization area (3) is to act as a barrier for cells and blood preventing to diffuse from the base component (4) into the brush-like fiber structure (2). It is, however, also possible to provide a stabilization area (3) that is porous and/or has specific pores to allow selective or non-selective cells to pass through.

In a further embodiment of the present invention, the stabilization area (3) of the device (1) is provided as a zone comprising at least one layer. The thickness of the zone is not specifically limited and can vary between broad ranges, e.g. between 1 nm and 1 mm.

In another preferred embodiment of the device of the invention (1), externally added components are included in either the at least one layer of highly oriented fibers (2) or the base component (4) or in both of them. Usually said components are dispersed throughout the fibrous layer(s) (2) and/or the base component (4). Said components can be cells of different origin. The function is to support the generation of cartilage material and to enhance to improve healing, integration and mechanical properties of the device (1).

The cells are preferably autologous cells, allogenous cells, xenogenous cells, transfected cells and/or genetically engineered cells.

Particularly preferred cells which can be present throughout the fiber layer(s) (2) are chondrocytes, chondral progenitor cells, pluripotent cells, tutipotent cells or combinations thereof. Examples for cells included in the base component (4) are osteoblasts, osteo-progenitor cells, pluripotent cells tutipotent cells and combinations thereof. In some instances it can be desired to include blood or any fraction thereof in the base component (4).

An example for another internally added components are pharmaceutical compounds including growth factors, engineered peptide-sequences, or antibiotics. An example for another internally added components are gelating compounds including proteins, glycoaminoglycanes, carbohydrates, or polyethyleneoxides. These components can be added as free components, or they can be immobilized within the device of claim 1 by chemical, physical, or entrapment methods to prevent the washingout.

The device of the present invention can be directly implanted in a defect, diseased, or deceased cartilaginous area such as articulating joints in humans and animals. Examples of these articulating joints are the cartilage areas in hip, elbow, and knee joints. Usually, implanting the device into a joint is made by surgical procedures. For example the insertion procedure can be as following:

In a first step, the defect area is cleaned and an osteochondral plug is removed with a chisel. Special equipment allows for exacting bottom and walls with regard to depths and widths. The prosthetic device as described in claim 1 is carefully pressed into position in such a manner that the upper edge of the base component (4) is on the same level with the calcified zone dividing the cartilage and the bone. The top surface of the fiber layer (2) should equal the height of the surrounding cartilage. Height differences may be exacted.

The operation might be either carried out in an open or in an arthroscopic manner.

As already mentioned above, the device (1) can be seeded with cells or added with additional substances or cells. Normally, seeding of the cells occurs after in-vitro cultivation according to methods established in the art. It is, however, also possible to harvest cells during the operational procedure from the patient, and seed the scaffold after the cells have been purified.

For special applications, it will be also possible to assemble the device of claim 1 intra operatively. I.e. the base component (4) is implanted first, and subsequently the fiber layer (2) is immobilized on to of the base component (4) under formation of the stabilization layer (3). The height of the fiber layer (2) is adjusted to the contour of the joint after the immobilization procedure e.g. by shaving or heat treatment.

The present invention is illustrated by means of the following examples.

Example 1

A prosthetic device is engineered from a porous interconnected cylindrical beta-tri-calcium-phosphate body sizing 5 mm in diameter and 10 mm in height, as subchondral anchor, and a 4 mm layer of oriented poly-hydroxy-ethyl-methacrylate (pHEMA) fibers with a diameter of 25 micrometer, as oriented fiber layer grafted to the anchor by a cement reaction. The vertical arrangement of the pHEMA fibers is random, but closely packed. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Subsequently, the anchor of the graft is soaked in a saline solution before the prosthetic device is inserted through the universal guide tool. No additional fixation of the prosthetic device is necessary due to the exact fit and the swelling of the fiber layer. Finally, the surface of the prosthetic device is resurfaced—if necessary—to match the exact curvature of the joint surface and the height of the surrounding articular surface.

Example 2

A prosthetic device is engineered from a porous interconnected cylindrical hydroxyapatite body sizing 8 mm in diameter and 15 mm in height, as subchondral anchor, and a 4 mm layer of oriented and chemically derivatized methylcellulose fibers with diameters ranging between 1 and 50 micrometers, as oriented fiber layer. The fiber layer is obtained by embroidery and chemically grafted to the anchor by embedding. The vertical arrangement of the methylcelluose is a well-defined 2-D pattern. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Subsequently, harvested bone marrow stromal cells are added to the ceramic anchor. Next, the prosthetic device is inserted through the universal guide tool. No additional fixation of the prosthetic device is necessary due to the exact fit and the swelling of the fiber layer. Finally, the surface of the prosthetic device is resurfaced—if necessary—to match the exact curvature of the joint surface and the height of the surrounding articular surface.

Example 3

A prosthetic device is engineered from a porous interconnected cylindrical beta-tri-calcium-phosphate and calcium sulfate composite body sizing 12 mm in diameter and 10 mm in height, as subchondral anchor, and a 5 mm mixed layer of highly oriented polypropylene and polyetheretherketone fibers with a diameters ranging 0.5 to 30 micrometer, as oriented fiber layer. The vertical arrangement of the fibers is random, but closely packed. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells and platelet rich plasma is added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface.

Example 4

A prosthetic device is engineered from a porous interconnected cylindrical beta-tri-calcium-phosphate body sizing 30 mm in diameter and 25 mm in height with a convex surface curvature, as subchondral anchor, and a 6 mm layer of highly oriented Pluronic fibers with a diameters about 10 micrometer, as oriented fiber layer. The vertical arrangement of the fibers is random and 5 to 80% of the fibers are crosslinked to its nearest neighbors. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Platelet rich plasma is added to the anchor, and the prosthetic device is inserted subsequently by the universal guide tool. No additional fixation of the prosthetic device is necessary due to the exact fit and the swelling behavior of the fiber layer. The surface of the prosthetic device is finally resurfaced to match the exact curvature of the joint surface and the height of the surrounding articular surface.

Example 5

A prosthetic device is engineered from a porous interconnected cylindrical beta-tri-calcium-phosphate body sizing 8 mm in diameter and 10 mm in height, as subchrondral anchor, and a 3 mm layer of highly oriented alginate fibers with diameters ranging between 1 and 30 micrometer, as oriented fibers layer. The vertical arrangement of the fibers is random and 50 to 95% of the fibers are crosslinked to its nearest neighbors. The fibers of the layer are embedded in a ceramic layer that acts as a barrier between the fiber layer and the anchor. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface. Finally, chondrocytes as cell suspension are added to the layer.

Example 6

A prosthetic device is engineered from a porous interconnected cylindrical calcium deficient hydroxy apatite (CDHA) body sizing 4 mm in diameter and 5 mm in height, as subchondral anchor and a 3 mm layer of highly oriented chitosan fibers with a diameters ranging between 0.5 and 50 micrometer, as oriented fiber layer. The vertical arrangement of the fibers is random. The fibers of the layer are embedded in a ceramic layer that acts as a selective barrier between the fiber layer and the anchor. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface.

Example 7

A prosthetic device is engineered from a porous interconnected cylindrical beta-tri-calcium-phosphate body sizing 10 mm in diameter and 10 mm in height, as subchondral anchor and a 3 mm layer of highly oriented polyethyleneglycol (PEG) fibers with a diameters ranging up to SO micrometer, as oriented fiber layer. The vertical arrangement of the fibers is according to a pre-defined pattern. About SO % of the fibers are crosslinked to its nearest neighbors. The fibers of the layer are embedded in a ceramic layer that acts as a barrier between the fiber layer and the anchor. The resulting prosthetic device is an ideal implant for cartilage repair.

A properly sized tubular chisel is introduced perpendicular to the defect site in the joint. In a first step in the implantation, the chisel is tapped into cartilage and the osseous base of the defect site. The defect size is exacted regarding depth and diameter to the specific dimensions of the prosthetic device. Bone marrow stromal cells are added to the anchor, and the prosthetic device is inserted subsequently by the universal guide tool. No additional fixation of the prosthetic device is necessary due to the exact fit. If necessary, the surface of the prosthetic device is finally resurfaced to match the exact curvature of the joint surface and the height of the surrounding articular surface. Finally, chondrocytes as cell suspension are added to the fiber layer.

Example 8

A prosthetic device is engineered from a porous interconnected cylindrical calcium deficient hydroxy apatite body sizing 4 mm in diameter and 5 mm in height, as subchondral anchor, and a 3 mm layer of highly oriented hyaluronic acid fibers mixed with collagen fibers with diameters for both materials ranging between 0.1 and 25 micrometer, as oriented fiber layer. The vertical arrangement of the fibers is random and about 70 to 100% of the fibers are crosslinked. The fibers of the layer are embedded in a ceramic layer that acts as a selective barrier between the fiber layer and the anchor. The resulting prosthetic device is an ideal implant for cartilage repair.

Autologous chondrocytes are added to layer and the device is are pre-cultivated in-vitro. For implantation, a properly sized tubular chisel is introduced perpendicular to the defect site in the joint. The chisel is tapped into cartilage and the osseous base of the defect site. The defect size is exacted regarding depth and diameter to the specific dimensions of the prosthetic device. Platelet Rich Plasma is added to the anchor, and the prosthetic device is inserted subsequently by the special guide tool. No additional fixation of the prosthetic device is necessary due to the exact fit.

The invention claimed is:

1. A prosthetic device for repairing or replacing cartilage or cartilage tissue (1) comprising:
   at least one layer consisting of at least partially oriented fibers (2),
   a base component (4) to anchor said at least one layer consisting of at least partially oriented fibers (2) in subchondral environment, and
   a stabilization area (3) provided between said at least one layer consisting of at least partially oriented fibers (2) and said base component (4),
   wherein said at least partially oriented fibers (2) are aligned essentially in parallel to the insertion axis of the prosthetic device that is in a direction perpendicular to a top surface of said base component and the at least one layer consisting of at least partially oriented fibers (2) form a brush-like structure,
   wherein more than 50% of said at least partially oriented fibers are aligned essentially in parallel to the insertion axis of the device.

2. The device according to claim 1, wherein the material of the at least partially oriented fibers (2) includes a mineral material, synthetic polymers or molecules, natural polymers or molecules, biotechnologically derived polymers or molecules, biomacromolecules, or any combination thereof.

3. The device according to claim 2, wherein the diameter of the at least partially oriented fibers (2) is in a range of 50 nm to 1 mm.

4. The device according to claim 3, wherein said fiber diameter is in a range of 1 μm to 250 μm.

5. The device according to claim 2, wherein the at least partially oriented fibers (2) have a liquid absorbing capacity in a range of 0.1% to 99.9%.

6. The device according to claim 5, wherein said liquid absorbing capacity is in a range of 20.0% to 99.0%.

7. The device according to claim 5, wherein the liquid is an aqueous solution and/or body fluids.

8. The device according to claim 1, wherein the base component (4) comprises a material used as a bone substitute.

9. The device according to claim 8, wherein said bone substitute is a mineral material, synthetic polymers or molecules, natural polymers or molecules, biotechnologically derived polymers or molecules, biomacromolecules, or any combination thereof.

10. The device according to claim 8, wherein said material is a synthetic ceramic containing at least one of the following components: calcium phosphate, calcium sulfate, calcium carbonate, or any mixture thereof.

11. The device according to claim 10, wherein said calcium phosphate contains at least one of the following components: di-calciumphosphatedihydrate ($CaHPO_4 \times 2H_2O$), dicalciumphosphate ($CaHPO_4$), alpha-tricalciumphosphate (alpha-$Ca_3(PO_4)_2$), beta-tricalciumphosphate (beta$Ca_3(PO_4)_2$), calcium deficient hydroxylapatite ($Ca_9(PO_4)_5(HPO_4)OH$), hydroxylapatite ($Ca_{10}(PO_4)_6OH_2$), carbonated apatite ($Ca_{10}(PO_4)_3(CO_3)_3 (OH)_2$) fluorapatite ($Ca_{10}(PO_4)_6(F,OH)_2$), chlorapatite ($Ca_{10}(PO_4)_6(Cl,OH)_2$), whitlockite (($Ca, Mg)_3(PO_4)_2$), tetracalciumphosphate ($Ca_4(PO_4)_2O$), oxyapatite ($Ca_{10}(PO_4)_6O$), beta-calciumpyrophosphate (beta-$Ca_2P_2O_7$), alpha-calciumpyrophosphate, gamma-calcium-pyrophosphate, octacalciumphosphate ($Ca_8H_2 (PO_4)_6 \times 5H_2O$).

12. The device according to claim 8, wherein said material is a synthetic ceramic containing metallic, semimetallic ions, and/or non-metallic ions, preferably magnesium, silicon, sodium, potassium, and/or lithium.

13. The device according to claim 8, wherein the material is a composite material comprising at least a polymer component and a mineral phase.

14. The device according to claim 8, wherein the bone substitute material is highly porous with interconnecting pores.

15. The device according to claim 8, wherein the shape of the base component (4) is round, cylindrical, or conical.

16. The device according to claim 15, wherein the diameter of the base component (4) ranges between 2 and 30 mm, with a height being 1 to 30 mm.

17. The device according to claim 15, wherein the diameter of the base component (4) ranges between 4 and 20 mm, with a preferred height being between 1 to 6 mm.

18. The device according to claim 1, wherein said stabilization area (3) is a zone comprising at least one layer.

19. The device according to claim 18, wherein said zone has a thickness of 1 nm to 1 mm.

20. The device according to claim 18, wherein said zone is porous.

21. The device according to claim 1, further comprising at least one externally added component.

22. The device according to claim 21, wherein said component is cells of different origin.

23. The device according to claim 22, wherein said cells are autologous cells, allogenous cells, xenogenous cells, transfected cells and/or genetically engineered cells.

24. The device according to claim 21, wherein chondrocytes, chondral progenitor cells, pluripotent cells, tutipotent cells or combinations thereof are present throughout the fiber layer(s) (2).

25. The device according to claim 21, wherein osteoplasts, osteo progenitor cells, pluripotent cells, tutipotent cells or combinations thereof are present throughout the base component (4).

26. The device according to claim 21, wherein blood or any fraction thereof is present throughout the base component (4).

27. The device according to claim 21, wherein pharmaceutical compounds are contained.

28. The device according to claim 1, wherein the device is adapted to be implanted in articulating joints in humans and animals.

29. The device according to claim 28 wherein the device regenerates articulator cartilagenous tissue.

30. The device according to claim 1, wherein more than 90% of said at least partially oriented fibers (2) are aligned essentially in parallel to the insertion axis of the device that is in a direction perpendicular to a top surface of said base component.

31. The device according to claim 1, wherein the stabilization area (3) is an absolute or selective cell barrier layer for preventing cells and blood from diffusing from the base component (4) into the brush-like fiber structure.

32. The device according to claim 5, wherein the at least partially oriented fibers (2) are designed to form a gel or transform to a gel-like state when absorbing liquid.

* * * * *